United States Patent
Rasche et al.

(10) Patent No.: US 7,964,586 B2
(45) Date of Patent: Jun. 21, 2011

(54) METHOD FOR OBTAINING A NATURAL MIXTURE OF CONJUGATED EQUINE ESTROGENS

(75) Inventors: Heinz-Helmer Rasche, Burgdorf (DE);
Kirsten Wilbrand, Wunstorf (DE);
Sabine Banschbach, Schwarmstedt (DE)

(73) Assignee: Abbott Products GmbH, Hannover (DE)

( * ) Notice: Subject to any disclaimer, the term of this patent is extended or adjusted under 35 U.S.C. 154(b) by 782 days.

(21) Appl. No.: 10/890,390

(22) Filed: Jul. 14, 2004

(65) Prior Publication Data

US 2005/0032767 A1    Feb. 10, 2005

Related U.S. Application Data

(60) Provisional application No. 60/491,530, filed on Aug. 1, 2003.

(30) Foreign Application Priority Data

Jul. 17, 2003   (EP) .................................. 03102215

(51) Int. Cl.
*A61K 31/56* (2006.01)
(52) U.S. Cl. ....................................................... 514/170
(58) Field of Classification Search ................... 514/170
See application file for complete search history.

(56) References Cited

U.S. PATENT DOCUMENTS

| | | | |
|---|---|---|---|
| 2,429,398 A | 10/1947 | Cook et al. | |
| 2,551,205 A | 5/1951 | Cook et al. | |
| 2,565,115 A | 8/1951 | Bates et al. | |
| 2,696,265 A * | 12/1954 | Beall et al. | 424/546 |
| 2,834,712 A | 5/1958 | Beall et al. | |
| 3,769,401 A * | 10/1973 | Thompson | 424/546 |
| 5,723,454 A * | 3/1998 | Ban et al. | 514/170 |
| 5,814,624 A | 9/1998 | Ban et al. | |
| 7,081,451 B2 * | 7/2006 | Ahnsorge et al. | 514/170 |
| 2004/0072814 A1 * | 4/2004 | Ban et al. | |

FOREIGN PATENT DOCUMENTS

| | | |
|---|---|---|
| CN | 1308083 | 8/2001 |
| WO | WO 98/08526 | 3/1998 |
| WO | WO 01/27134 A1 | 4/2001 |
| WO | WO 03/048183 A2 | 6/2003 |

* cited by examiner

*Primary Examiner* — Barbara P Badio
(74) *Attorney, Agent, or Firm* — Crowell & Moring LLP

(57) ABSTRACT

A method for obtaining an extract containing the natural mixture of conjugated equine estrogens in which a mixture of conjugated estrogens obtained by solid-phase extraction from pregnant mares' urine is depleted in phenolic urine contents and in non-conjugated lipophilic compounds selected from the group consisting of non-conjugated flavonoids, non-conjugated isoflavonoids, non-conjugated norisoprenoids, non-conjugated steroids, in particular androstane and pregnane steroids, and comparable non-conjugated compounds.

26 Claims, No Drawings

US 7,964,586 B2

METHOD FOR OBTAINING A NATURAL MIXTURE OF CONJUGATED EQUINE ESTROGENS

CROSS REFERENCE TO RELATED APPLICATIONS

This application claims priority from U.S. provisional patent application No. 60/491,530, filed Aug. 1, 2003. Convention priority is also claimed based on European patent application no. 03102215.5, filed Jul. 17, 2003.

BACKGROUND OF THE INVENTION

The present invention relates to obtaining a natural mixture of conjugated equine estrogens which is depleted in phenolic urine contents and in non-conjugated lipophilic compounds from the group comprising non-conjugated flavonoids, non-conjugated isoflavonoids, non-conjugated norisoprenoids, non-conjugated steroids, in particular androstane and pregnane steroids, and comparable non-conjugated compounds.

Estrogens are used in medicine for hormone replacement therapy. In particular, estrogen mixtures are used for the treatment and prophylaxis of the disorders of the climacteric period which occur in women after natural or artificial menopause. In this case, natural mixtures of conjugated estrogens such as are found in the urine of pregnant mares, hereafter referred to as natural mixtures of conjugated equine estrogens, have proved particularly effective and readily compatible.

The dissolved solids content in the urine of pregnant mares (=pregnant mares' urine, abbreviated hereafter as "PMU") can naturally fluctuate within wide ranges, and may generally lie in a range of 40 to 90 g dry matter per liter. In addition to urea and other usual urine contents, phenolic constituents are contained in the solids content of the PMU in quantities of about 2 to 5% by weight relative to the dry matter. These phenolic constituents include cresols and dihydro-3,4-bis[(3-hydroxyphenyl)methyl]-2(3H)-furanone, known as HPMF. These may be present in free or conjugated form. The PMU contains a natural mixture of estrogens which is largely present in conjugated form, e.g. as sulfuric acid semi-ester sodium salt (abbreviated hereafter as "sulfate salt"). The content of conjugated estrogens (calculated as estrogen sulfate salt) may be between 0.1 and 0.5% by weight, relative to the dry matter. In addition, further lipophilic compounds may be present in the solids content of the PMU, the quantities of which compounds can fluctuate within wide ranges and cannot be predicted. These lipophilic compounds originate predominantly from the plants ingested as food by the pregnant mares and comprise above all various flavonoid, isoflavonoid and norisoprenoid derivatives and comparable compounds, such as for example formononetin, genistein, daidzein, biochanin A, equol and coumestrol. These lipophilic compounds originally of plant origin may be present in the urine in conjugated or in free (non-conjugated) form. The lipophilic constituents furthermore occurring in the solids content of the PMU also include non-conjugated steroid derivatives; of these in particular the androstane and pregnane steroids, but also non-conjugated estrogen derivatives, should be mentioned.

Extracts containing natural mixtures of conjugated estrogens are usually obtained either by means of a solid-phase extraction method or by a method based on various liquid-liquid extraction steps with organic solvents which are not miscible, or only slightly miscible, with water. Generally speaking, in order to be able to be used as active substance constituent for pharmaceuticals, the natural mixture of conjugated estrogens which is obtained must meet certain pharmaceutical specifications, for example meet the specification laid down in the USP (United States Pharmacopeia) or European Pharmacopoeia. For example, certain limit values must be observed with regard to the content of conjugated estrogens relative to the dry matter.

U.S. Pat. Nos. 2,551,205 and 2,429,398 describe a method for preparing a water-soluble estrogen preparation from PMU, in which first an aqueous concentrate is obtained by adsorption on activated carbon or other suitable adsorber materials, elution with a water-miscible organic solvent, such as pyridine, and subsequent removal of the solvent, which concentrate contains the major part of the water-soluble estrogen constituents of the PMU originally used. Whereas in U.S. Pat. No. 2,429,398 the concentrate is further purified by extraction with benzene and/or ether, U.S. Pat. No. 2,551,205 discloses acidulating the concentrate to a pH value of between 2 and 6, preferably between 4 and 5, and then rapidly extracting it with a organic solvent which is only slightly miscible with water selected from the group consisting of aliphatic, aromatic or alicyclic hydrocarbons (e.g. hexane, benzene, toluene, cyclohexane) or chlorinated hydrocarbons (e.g. chloroform, ethylene dichloride, trichloroethylene, carbon tetrachloride, chlorobenzene), in order to separate undesirable substances such as fats, oils, free phenolic constituents and the non-conjugated steroids by transfer into the organic phase. Finally, the aqueous phase is stabilized by neutralization. U.S. Pat. No. 2,551,205 recommends further purifying the resulting extract by subsequent extraction steps and precipitation operations. Overall, after carrying out the method described in U.S. Pat. No. 2,551,205, a yield of only about 80% of the estrogen constituents of the concentrate used is obtained.

U.S. Pat. No. 2,565,115 describes extraction of the conjugated estrogens from PMU with acetone. No statement is made about the purity of the resulting estrogen fraction.

U.S. Pat. No. 2,696,265 describes a method in which initially the estrogens are extracted with an aliphatic alcohol or ketone, such as hexanol, cyclohexanol or cyclohexanone. The estrogens pass into the organic phase and are then further purified; inter alia, an aqueous phase containing the estrogens is adjusted to a pH value of 4 with hydrochloric acid and extracted with ethylene dichloride.

U.S. Pat. No. 2,834,712 discloses a method for preparing estrogen mixtures of significant purity and low toxicity which is based on a large number of individual extraction steps with different solvents and the setting of different pH values. In that method, large volumes of solvents such as hexane and benzene are used. Thus for example in one step an already-purified concentrate is dissolved in water, adjusted to a pH value of approximately 5.0 with hydrochloric acid, and extracted with benzene and then with ether, in order to separate out the phenolic constituents.

International patent application no. WO 01/27134 describes a comparatively simple method of extracting conjugated estrogens from PMU. After the addition of a salt, such as sodium chloride, the PMU is extracted with at least the same volume percent of an organic solvent, such as ethyl acetate, whereupon the conjugated estrogens pass into the organic phase. The organic phase is separated and dried in order to obtain the extract. No statements are made in WO 01/27134 about the purity of the extract of conjugated estrogens which is obtained.

With the liquid-liquid-extraction method described above and known from the prior art, however, a number of problems occur, such as vigorous foaming, sediment formation, emulsification and poor phase separation. Generally several extraction steps are required, which results in losses and only partial recovery of the estrogen content. Furthermore, these extraction methods require large volumes of solvents, some of which may be hazardous. Furthermore, in the patent specifications listed above no statements are made either about the content of non-conjugated lipophilic constituents, such as for example non-conjugated flavonoid, isoflavonoid and norisoprenoid derivatives and comparable non-conjugated compounds, or also non-conjugated steroids, in particular androstane and pregnane steroids, in the resulting products, or about separation of these constituents. These methods known from the prior art either provide no satisfactory results with regard to the yield or with regard to the purity of the extract obtained, measured by the total hormone content obtained relative to the dry matter, or they are based on a large number of different method steps and the use of large volumes of organic solvents, some of which may be hazardous.

Furthermore various solid-phase extraction methods are known from the prior art for obtaining a natural mixture of conjugated equine estrogens largely depleted in phenolic urine contents.

Thus, international patent application no. WO 98/08526 describes a method with which a largely cresol-free and HPMF-free mixture, which is depleted in phenolic urine contents and contains the natural estrogen content of the PMU practically completely can be obtained in a solid-phase extraction on a semipolar, in particular non-ionic semipolar, polymeric adsorption resin. International patent application no. WO 98/08526 describes a similar method in which silica gel is used as adsorber material in the solid-phase extraction. Also, Chinese patent application CN 1308083 describes a comparable method in which polar adsorption resins containing cyano groups are used. Furthermore, published U.S. patent application Ser. No. US 2002/0156303 describes a method in which the PMU before purification over a polystyrene adsorption resin is first treated with an alkaline solvent and is pre-purified by filtration. The resulting extracts are suitable as starting materials for preparing pharmaceuticals which contain the natural mixture of conjugated estrogens from PMU as active substance constituent.

The pharmaceutical specification requirements laid down, for example the limit values to be observed with regard to the content of conjugated estrogens relative to the dry matter, are normally met by the mixtures of conjugated estrogens obtained from PMU in accordance with the method of WO 98/08526 or the method of WO 98/08525. In particular, it is possible, using the method disclosed therein, to obtain a largely cresol-free and HPMF-free product which is depleted in phenolic urine contents. It has however turned out that in addition to the desired content of conjugated estrogens, the resulting dry matter also may contain non-conjugated lipophilic compounds. The non-conjugated lipophilic compounds include, for example, various non-conjugated flavonoid, isoflavonoid and norisoprenoid derivatives and comparable non-conjugated compounds, such as for example formononetin, genistein, daidzein, biochanin A, equol and coumestrol, but also non-conjugated steroids, in particular androstane and pregnane steroids, and non-conjugated estrogens. The foregoing list should not be regarded as definitive. The presence of these non-conjugated lipophilic compounds in the mixture of conjugated estrogens obtained from the PMU cannot be standardized, but both the content and the composition of the free and conjugated lipophilic compounds varies, for example, depending on the feed ingested by the pregnant mares.

Although the composition of the natural mixture of conjugated equine estrogens does not change due to the additional presence of the non-conjugated lipophilic compounds, the content of the conjugated equine estrogens relative to the dry matter can be reduced. A higher concentration of the active substances, i.e. the conjugated equine estrogens, in the product extract could be achieved by deliberate separation of the non-conjugated lipophilic constituents. Furthermore, separation of the non-conjugated lipophilic compounds ensures a more uniform composition of individual extract batches, since in this way the non-conjugated lipophilic constituents, the content and composition of which in the PMU can vary depending on the seasonally changing type of food ingested by the pregnant mares, are eliminated, and thus the resulting extracts all have a comparable content of conjugated equine estrogens relative to the dry matter. Furthermore, separation of the non-conjugated lipophilic compounds may be advantageous in order to obtain a uniform physiological activity spectrum. For example, it may be useful to separate out possibly present, non-conjugated lipophilic compounds, which may themselves have inherent physiological effects, from the natural mixture of conjugated equine estrogens.

One possible way of separating the undesirable, non-conjugated lipophilic compounds would be, for example, to subject the natural mixtures of conjugated equine estrogens obtained using the known solid-phase extraction methods set forth above to a separate liquid-liquid extraction with a suitable organic solvent which specifically extracts the undesirable, non-conjugated lipophilic compounds, without resulting in a loss of conjugated equine estrogens. Such a method is broadly described in the pending international patent application PCT/EP 03/50703.

SUMMARY OF THE INVENTION

The object of the present invention is to provide a technically and economically optimum method for obtaining a natural mixture of conjugated equine estrogens, the mixture being largely depleted both in phenolic urine contents and in non-conjugated lipophilic compounds, in particular in non-conjugated flavonoid, isoflavonoid and norisoprenoid derivatives.

A particular object of the invention is to provide a method which, compared to the already known method for obtaining natural mixtures of conjugated equine estrogens, does not require any additional operating steps.

Yet another object of the invention is to provide a method in which the depletion both in phenolic urine contents and in non-conjugated lipophilic compounds takes place during a solid-phase extraction.

A further object of the invention is to provide a method which is based on only a few method steps and yields an extract of conjugated equine estrogens which has a comparatively high content of conjugated estrogens relative to the dry matter.

An additional object of the invention is to provide a method which makes it possible in a simple manner to obtain a natural mixture of conjugated estrogens from pregnant mares' urine even when the urine contains changing and possibly elevated amounts of non-conjugated lipophilic compounds.

A still further object of the invention is to provide an optimized method for solid-phase extraction, so that the resulting natural mixture of conjugated equine estrogens has a good active-substance content and meets required pharmaceutical specifications.

In particular, the method of the invention should observe the necessary limit values regarding the content of conjugated estrogens relative to the dry matter.

These and other objects are achieved in accordance with the present invention by providing a method for obtaining a natural mixture of conjugated estrogens from pregnant mares' urine, comprising:

contacting a urine with an amount of a polymeric adsorption resin sufficient to adsorb the mixture of conjugated estrogens contained in the urine, and separating a resulting polymeric adsorption resin loaded with the mixture of conjugated estrogens from the rest of the urine;

washing the polymeric adsorption resin loaded with the mixture of conjugated estrogens with a washing water which has been adjusted to a pH value of at least 12.0;

contacting the washed adsorption resin with a sufficient amount of an elution liquid to desorb the mixture of conjugated estrogens loaded thereon, and separating an eluate containing the natural mixture of conjugated estrogens from the adsorption resin;

wherein:

the natural mixture of conjugated equine estrogens is depleted in phenolic urine contents and in non-conjugated lipophilic compounds, and comparable non-conjugated compounds, and the separated eluate is a one-phase or two-phase mixture containing:

(i) water, and (ii) at least one water-immiscible or only slightly water-miscible organic solvent suitable for the elution of non-conjugated lipophilic compounds; and if the separated eluate is a two-phase mixture, further comprising separating the phases and recovering an aqueous phase containing the natural mixture of conjugated estrogens.

A method has now been found with which, in a surprisingly simple manner, a mixture of conjugated equine estrogens which is depleted in phenolic urine contents and is largely cresol-free and HPMF-free can be obtained from PMU and at the same time is also largely depleted in non-conjugated lipophilic compounds, in particular in non-conjugated flavonoid, isoflavonoid and norisoprenoid derivatives, even if the PMU contains changing and possibly elevated amounts of non-conjugated lipophilic compounds.

Some steps of the method according to the invention are based on the method described in WO 98/08526, which serves for obtaining a natural mixture of conjugated estrogens depleted in phenolic urine contents from the PMU. Furthermore, the method according to the invention is based on the method described in international patent application WO 03/048183, with which, even when using aged PMU which has possibly elevated contents of free estrogens, a natural mixture of conjugated estrogens can be obtained which meets the required pharmaceutical specifications.

Accordingly, the invention relates to a method for obtaining a natural mixture of conjugated estrogens from pregnant mares' urine, in which a) a urine, which optionally represents a urine freed of mucilaginous substances and solids, a reduced concentrate of this urine or a reduced urine retentate obtained by membrane filtration of this urine, is contacted with an amount of a polymeric adsorption resin sufficient for the adsorption of the mixture of conjugated estrogens contained in the urine, and a polymeric adsorption resin loaded with the mixture of conjugated estrogens is separated from the rest of the urine, and b) the polymeric adsorption resin loaded with the mixture of conjugated estrogens is washed with washing water set to a pH value of at least 12.0, in particular 12.5 to 14.0, and c) optionally an intermediate washing operation is carried out, in which the polymeric adsorption resin loaded with the mixture of conjugated estrogens is washed with water, and d) the washed adsorption resin is contacted with an amount of an elution liquid, sufficient for the desorption of the mixture of conjugated estrogens adsorbed thereon, and e) an eluate containing the natural mixture of conjugated estrogens is separated from the adsorption resin and optionally reduced, the method according to the invention being distinguished from the methods of the prior art:

in that the natural mixture of conjugated equine estrogens obtained is depleted in phenolic urine contents and in non-conjugated lipophilic compounds selected from the group consisting of non-conjugated flavonoids, non-conjugated isoflavonoids, non-conjugated norisoprenoids, non-conjugated steroids, in particular androstane and pregnane steroids, and comparable non-conjugated compounds, and in that a one- or two-phase mixture, containing (i) water which is optionally set to a pH value in the alkaline range, and (ii) at least one organic solvent suitable for the elution of non-conjugated lipophilic compounds from the above group, which is not miscible, or only slightly miscible, with water, and optionally (iii) at least one water-miscible organic solvent selected from the group consisting of water-miscible ethers, lower alkanols and lower aliphatic ketones, and also mixtures of the aforementioned solvents, is used as elution liquid in method step (d), and that, if the optionally reduced eluate obtained in method step e) represents a two-phase mixture, the aqueous phase of the resulting eluate consisting of two phases is separated, and an aqueous phase containing the natural mixture of conjugated estrogens is obtained and is optionally reduced.

The batch preparation, the known method steps a), b), d) and e) and also the use of the eluate obtained in method step e), which contains a mixture of natural conjugated estrogens, are already described generally in international patent application WO 98/08526 as method steps a), b) and c) and are thus familiar to the person skilled in the art from this published patent application. The known method step c) of the present invention is described generally in international patent application WO 03/048183 as "intermediate washing" and is thus familiar to the person skilled in the art from this published patent application. The contents of WO 98/08526 and WO 03/048183 are incorporated herein by reference. Further details of the general procedure and materials which can be used are compiled in the examples of the present application.

For example, according to WO 98/08526, semipolar, in particular non-ionic semipolar, adsorption resins are used. Furthermore, according to the method of the present invention it is surprisingly also possible to use other adsorption resins together with the method according to the invention, without the product quality or the pharmaceutical specification to be met being adversely affected. Thus in the context of the present invention polymeric adsorption resins are suitable for use as adsorbent for the method according to the invention. The polymeric adsorption resins usable in the context of the present invention will be explained in greater detail further below in the examples section of the description.

According to the invention, with the present method a natural mixture of conjugated equine estrogens is obtained which is depleted both in phenolic urine contents such as cresols and HPMF and in non-conjugated lipophilic compounds from the group comprising non-conjugated flavonoids, non-conjugated isoflavonoids, non-conjugated norisoprenoids, non-conjugated steroids, in particular androstane and pregnane steroids, and comparable non-conjugated compounds.

After performing the known method steps (a) to (c), for this in method step (d) the washed adsorption resin loaded with the mixture of conjugated estrogens is treated with an amount of an elution liquid sufficient to elute the mixture of conjugated estrogens. According to the invention, for this there is used as elution liquid in method step (d) a one- or two-phase mixture which contains (i) water which is optionally set to a pH value in the alkaline range, and (ii) at least one organic solvent suitable for the elution of non-conjugated lipophilic compounds from the group comprising non-conjugated flavonoids, non-conjugated isoflavonoids, non-conjugated norisoprenoids, non-conjugated steroids, in particular androstane and pregnane steroids, and comparable non-conjugated compounds which is not miscible, or only slightly miscible, with water, and optionally (iii) at least one water-miscible organic solvent selected from the group consisting of water-miscible ethers, lower alkanols and lower aliphatic ketones, and also mixtures of the aforementioned solvents.

In a preferred embodiment of the present invention, the elution liquid in method step (d) is a one- or two-phase mixture which contains (i) water which is optionally adjusted to a pH value in the alkaline range, and (ii) at least one organic solvent suitable for the elution of non-conjugated lipophilic compounds selected from the group consisting of non-conjugated flavonoids, non-conjugated isoflavonoids, non-conjugated norisoprenoids, non-conjugated steroids, in particular androstane and pregnane steroids, and comparable non-conjugated compounds which are not miscible, or only slightly miscible, with water, and (iii) at least one water-miscible organic solvent selected from the group consisting of water-miscible ethers, lower alkanols and lower aliphatic ketones, and also mixtures of the aforementioned solvents.

The one- or two-phase mixture used as elution liquid in method step (d) contains water (i) which is optionally set to a pH value in the alkaline range.

If the elution liquid used in method step (d) is a one-phase mixture, the pH value of such water-containing elution liquids lies in the neutral to alkaline range up to pH 13 and may advantageously be in the range between pH 7 and 10. Organic solvents which are stable in the pH range used are selected as solvent components in the water-containing elution liquid. The desired pH value of the water-containing, one-phase elution liquid is set by adding a corresponding amount of a water-soluble inert basic substance, preferably an inorganic base, for instance an alkali metal or alkaline earth metal hydroxide, in particular sodium hydroxide.

If the elution liquid used in method step (d) is a two-phase mixture, the pH value of the aqueous phase of such water-containing elution liquids after thorough mixing of both phases lies in the neutral to alkaline range up to pH 13 and may advantageously be in the range of between pH 7 and 10. Where the aqueous phase of such two-phase elution liquids contains an organic solvent component, organic solvents which are stable in the pH range used are selected as the solvent component. The desired pH value of the aqueous phase of two-phase elution liquids is set by adding a corresponding amount of a water-soluble inert basic substance, preferably an inorganic base, for instance an alkali metal or alkaline earth metal hydroxide, in particular sodium hydroxide.

In addition to water (i) which is optionally rendered alkaline, the one- or two-phase mixture used as elution liquid in method step (d) contains at least one organic solvent (ii) suitable for the elution of non-conjugated lipophilic compounds selected from the group consisting of non-conjugated flavonoids, non-conjugated isoflavonoids, non-conjugated norisoprenoids, non-conjugated steroids, in particular androstane and pregnane steroids, and comparable non-conjugated compounds. Furthermore, the suitable organic solvent (ii) should be immiscible, or only slightly miscible, with water, "only slightly miscible" meaning that at most 6% by volume dissolved organic solvent is present in the aqueous phase. Examples of suitable organic solvents (ii) for eluting non-conjugated lipophilic compounds in the context of the method of the invention include, for example, the following organic solvents with 1 to 10 C atoms, which may be arranged in a straight-chain, branched or cyclic configuration: $C_4$-$C_{10}$ alcohols (such as for example butanol, hexanol, cyclohexanol and pentanol), $C_1$-$C_{10}$ esterified acids (such as for example ethyl acetate, methyl acetate, propyl acetate, isopropyl acetate, butyl acetate, amyl acetate, ethyl methyl malonate, dimethyl phosphonate), $C_3$-$C_{10}$ aldehydes and $C_4$-$C_{10}$ ketones (such as for example butanone, pentanone, hexane-2,4-dione, hexanedial, cyclohexanecarbaldehyde, butane-1,2,4-tricarbaldehyde, methyl phenyl ketone and the like), or generally $C_3$-$C_{10}$ alkoxy compounds, $C_3$-$C_{10}$ ethers (diethyl ether, methyl tert.butyl ether), $C_3$-$C_6$ nitriles and $C_1$-$C_3$ haloalkanes (methylene chloride), and also mixtures of two or more of the aforementioned solvents. In particular, $C_1$-$C_4$-alkyl acetates, butanol, cyclohexanol, hexanol, diethyl ether, methylene chloride, methyl-tert.butyl ether and mixtures of two or more of the aforementioned solvents may be used as water-immiscible or only slightly water-miscible organic solvents (ii) suitable for the elution of non-conjugated lipophilic compounds within the scope of the present invention. Of this selection, $C_1$-$C_4$-alkyl acetates, and in particular ethyl acetate and/or isopropyl acetate, represent the preferred water-immiscible or only slightly water-miscible organic solvents (ii) suitable for eluting non-conjugated lipophilic compounds.

Furthermore, the one- or two-phase mixture used according to the invention as elution liquid in method step (d) optionally contains at least one water-miscible organic solvent (iii) selected from the group consisting of water-miscible ethers, lower alkanols and lower aliphatic ketones, and also mixtures of two or more of the aforementioned solvents. Suitable ether constituents of the elution liquid include water-miscible cyclic ethers, such as tetrahydrofuran or dioxane, but also water-miscible open-chain ethers, such as ethylene glycol dimethyl ether (=monoglyme), diethylene glycol dimethyl ether (=diglyme) or ethyloxyethyloxy ethanol (=Carbitol). Suitable lower alkanols include water-miscible alkyl alcohols with 1 to 4, preferably 1 to 3, carbon atoms, in particular ethanol or isopropanol. Suitable lower aliphatic ketones include water-miscible ketones with 3 to 5 carbon atoms, in particular acetone. Elution liquids in which the water-miscible organic solvent (iii) is acetone, ethanol or a mixture of acetone and ethanol have proved particularly useful.

In one preferred configuration of the invention, the one- or two-phase mixture used as the elution liquid in method step (d) contains, in addition to water (i) which is optionally rendered alkaline, preferably ethyl acetate and/or isopropyl acetate as the water-immiscible or only slightly water-miscible solvent (ii) suitable for eluting non-conjugated lipophilic compounds, and a $C_1$-$C_4$-alkyl acetate, acetone and/or ethanol as the water-miscible organic solvent (iii).

In a further preferred embodiment of the invention, the one- or two-phase mixture used as elution liquid in method step (d) contains, in addition to water (i) which is optionally rendered alkaline, ethyl acetate as the water-immiscible or slightly water-miscible organic solvent (ii) suitable for eluting non-conjugated lipophilic compounds, and acetone as the water-miscible organic solvent (iii).

The one- or two-phase mixture used according to the invention as the elution liquid in method step (d) may have a volume ratio of water (i) to the water-immiscible or only slightly water-miscible organic solvent (ii) in the range of 5:1 to 1:5. In particular, a volume ratio in the range of 2:1 to 1:2 is considered advantageous.

Furthermore, the one- or two-phase mixture used in method step (d) as elution liquid may have a volume ratio of water (i) to the water-miscible organic solvent (iii) in the range of 4:1 to 1:5. Preferably a volume ratio in the range of 2:1 to 1:3 is considered advantageous.

In particular, the one- or two-phase mixture used in method step (d) as elution liquid may have a volume ratio of the total volume of water (i) together with the water-immiscible or only slightly water-miscible organic solvent (ii) in a ratio to the water-miscible organic solvent (iii) in the range of 5:1 to 1:5, preferably in the range of 2:1 to 1:2.

In an especially preferred embodiment of the present invention, the one- or two-phase mixture used in method step (d) as elution liquid is composed of (i) water, (ii) $C_1$-$C_4$-alkyl acetate, preferably ethyl acetate and/or isopropyl acetate, as the water-immiscible or only slightly water-miscible organic solvent, and (iii) acetone and/or ethanol as the water-miscible organic solvent in a volume ratio in the range from 1:1:1 to 1:1:2. In particular, a one-phase mixture is used in method step (d) as elution liquid, which mixture is composed of (i) water, (ii) ethyl acetate as water-immiscible or only slightly water-miscible solvent and (iii) acetone as the water-miscible organic solvent in a volume ratio of 1:1:1.4.

If a two-phase mixture is used in method step (d) as the elution liquid, it is recommended to mix the two phases together well immediately before charging on to the column.

The volume of elution liquid used may be approx. 3 to 10, in particular approx. 4 to 6 bed volumes per bed volume of polymeric adsorption resin. Advantageously, the elution liquid is passed through a reactor containing the adsorption resin loaded with the estrogen mixture at such a flow rate that the contact time is sufficient for complete elution of the mixture of conjugated estrogens. When using a one-phase mixture of water, ethyl acetate and acetone in a volume ratio of 10:10:14, for instance, flow rates of 3 to 10, preferably 5 to 7, parts by volume elution liquid per 1 part per volume adsorption resin per hour are suitable.

Advantageously, the elution is carried out at a temperature in the range from approx. 20° C. to approximately 80° C., preferably at temperatures between approximately 30° C. and 50° C. If desired, the flow rate is regulated by operating at slightly elevated pressure, e.g. at an excess pressure of up to 0.2 bar, and the eluate is collected in several fractions.

The contents of conjugated estrogens, phenolic urine contents such as cresols and HPMF and non-conjugated lipophilic compounds in the individual eluate fractions may be determined in known manner by high-performance liquid chromatography (abbreviated to "HPLC") or alternatively by gas chromatography (abbreviated to "GC").

Upon elution, in method step e) initially a slightly-colored to colorless, practically estrogen-free preliminary fraction is obtained, the amount of which corresponds generally to approximately one bed volume. The bulk of the conjugated estrogens, for instance between 80 and 99% of the conjugated estrogens present in the starting PMU, is in the subsequent dark-yellow-brown colored main eluate fractions, the amount of which is generally 2 to 4 bed volumes. Generally only traces of conjugated estrogens are contained in the subsequent last fractions. If succeeding fractions are obtained which still have a content of conjugated estrogens of above 10% by weight relative to dry matter and less than 0.6% by weight relative to dry matter of cresols and HPMF, these may be combined with the estrogen-rich main eluate for further processing.

The eluate obtained in method step (e) may be a one- or two-phase mixture. Even when using a one-phase mixture as elution liquid, due to the displacement of the water present on the adsorption resin column before the elution from the column and the shift in the volume ratios of the resulting aqueous and organic phases, the eluate may consist of two phases. If desired, the one- or two-phase eluate obtained in method step (e) may be reduced or concentrated further in known manner. In particular, if the eluate obtained in method step (e) is a one-phase one, the eluate is reduced, so that preferably the water-miscible organic solvent (iii) is separated until the reduced eluate represents a two-phase mixture.

According to the invention, if the optionally reduced eluate obtained in method step (e) represents a two-phase mixture, in a method step (f) the aqueous phase of the resulting eluate consisting of two phases is separated, and an aqueous phase containing the natural mixture of conjugated estrogens is obtained. To this end, the resulting two-phase eluate is allowed to stand in order to separate the phases. The phase separation may take from 10 min up to 24 hours, depending on the volumes obtained, but preferably the phases are allowed to stand for 5 to 10 hours. When the aqueous phase and the organic phase have separated from each other, the aqueous phase is collected and kept for re-use, while the organic phase is discarded.

After the separation of the organic phase from the aqueous phase, in method step (f) an aqueous phase containing the natural mixture of conjugated estrogens is obtained. This aqueous phase contains the natural mixture of conjugated estrogens occurring in the PMU in addition to only a small proportion of the content of phenolic urine contents, such as cresols and HPMF, originally present in the PMU and also in addition to only an extremely low content of non-conjugated lipophilic constituents originally present in the PMU. If desired, this aqueous phase can be reduced or concentrated further in known manner, in order to obtain a concentrate largely freed of organic solvent which is suitable for further processing. Thus, for example, the remaining residues of organic solvent can be distilled off from the resulting aqueous phase. The distillation means that the dry matter content of the aqueous extract phase can also be set to a concrete value, preferably to a dry matter content in the range between 5 and 15%, in particular to a dry matter content of about 9%. Following this, to stabilize the resulting natural mixture of conjugated equine estrogens, the pH value of the aqueous extract solution can be adjusted to a value in the alkaline range, preferably in the range between 8 and 13, particularly preferably to a value between 9 and 12. Bases suitable for adjusting the pH value include those typically used to adjust pH values, for example 1N NaOH or $Na_2CO_3$.

The aqueous phase obtained according to the invention in method step (f), which has optionally been still further worked up or concentrated, can serve as the starting material for preparing medicaments containing the natural mixture of conjugated equine estrogens. If desired, an eluent-free solids mixture can be produced by a suitable drying process, such as spray-drying or fluidized-bed drying. If the natural mixture of conjugated estrogens is to be used for the production of solid medicaments, it may be desirable to admix a solid excipient to the aqueous phase containing the conjugated estrogens before concentration or drying in order to obtain a solids mixture containing the conjugated estrogens and excipients. For example, the aqueous phase containing the conjugated estrogens may be sprayed onto a solid excipient such as cellulose in a fluidized bed. Both the aqueous phase containing the estrogen mixture and a concentrate or dried solids product prepared therefrom can be incorporated in known manner into solid or liquid galenic preparations such as, for example, tablets, coated tablets, capsules or emulsions. These galenic formulations can be prepared by known methods using conventional solid or liquid excipients, such as starch, cellulose, lactose or talcum or liquid paraffins, and/or using conventional pharmaceutical auxiliaries, for example tablet disintegrating agents, solubilizers or preservatives. Thus the product containing the conjugated estrogens can be mixed with the pharmaceutical excipients and auxiliaries in known manner and the mixture converted into a suitable dosage form.

In the solid-phase extraction method described according to the invention, a natural mixture of conjugated equine estrogens is obtained from a urine, which optionally represents a urine freed of mucilaginous substances and solids, a reduced concentrate of such a urine or a reduced urine retentate obtained by membrane filtration of such a urine, the mixture in a simple method being largely depleted both in phenolic urine contents, such as in particular cresols and HPMF, and being depleted in a plurality of non-conjugated lipophilic compounds. The non-conjugated lipophilic compounds which are separated include, in particular, non-conjugated flavonoids, non-conjugated isoflavonoids, non-conjugated norisoprenoids and non-conjugated steroids, in this case in particular non-conjugated androstane and non-conjugated pregnane derivatives.

Compared with the known solid-phase extraction methods, the solid-phase extraction method according to the invention yields a natural mixture of conjugated equine estrogens which is very largely depleted both in phenolic urine contents and in non-conjugated lipophilic compounds, the method according to the invention getting by without additional working steps, since the depletion in non-conjugated lipophilic compounds also takes place as early as during the solid-phase extraction.

In the method known from WO 98/08526, a portion of the non-conjugated lipophilic compounds, for example the isoflavone equol, is washed out in method step b), whereas other non-conjugated lipophilic compounds, for example formononetin, pass on into the eluate and may possibly have to be separated by a subsequent liquid-liquid extraction. Something similar also applies for the non-conjugated, i.e. free, steroid hormones, which likewise can be detected in certain proportions in the eluate. It is therefore to be regarded as extremely surprising that a one-phase or even two-phase mixture of water, a water-immiscible or only slightly water-miscible organic solvent, and also optionally a water-miscible organic solvent such as lower ethers, alkanols or ketones, can be used for quantitatively eluting the conjugated estrogens adsorbed on a polymeric adsorption resin, and the resulting, optionally reduced eluate can be separated into two phases, the—completely eluted—conjugated estrogens being almost exclusively in the aqueous phase again, whereas the undesirable, non-conjugated lipophilic compounds are in the organic phase and thus can readily be separated.

Furthermore, the method according to the invention yields an extract of conjugated equine estrogens which has a comparatively high content of conjugated estrogens relative to dry matter. Thus it is possible in a simple manner, using the method of the present invention, to obtain a natural mixture of conjugated estrogens from pregnant mares' urine even when the urine contains changing and possibly elevated amounts of non-conjugated lipophilic compounds, without having to have the solid-phase extraction succeeded by further purification steps.

The natural mixture of conjugated equine estrogens which is depleted in non-conjugated lipophilic constituents and in phenolic urine contents which is obtained as active-substance extract by the method according to the invention is distinguished from the active-substance extracts obtained by the known solid-phase extraction method by a significant optimization of the pharmaceutical specification, as was established according to the invention.

It must be regarded as extremely surprising that such an improvement in the quality of the active-substance extract obtained can be brought about by the change according to the invention to the already-known solid-phase extraction method, even if the pregnant mares' urine delivering the natural mixture of conjugated estrogens contains differing and changing amounts of non-conjugated lipophilic constituents. In particular, it is very surprising that the proportion of non-conjugated lipophilic compounds, which can fluctuate greatly both in terms of quantity and composition according to the PMU used, can be reduced by the method according to the invention so reliably that in method step (f) a mixture of natural conjugated equine estrogens which meets the stringent requirements for pharmaceutical specification, for example the requirements drawn up in accordance with the USP or the European Pharmacopoeia can be obtained as aqueous phase.

The method according to the invention, as already described in detail above, has a number of advantages and improvements compared with the prior art. Thus the invention makes it possible also to use PMU containing changing quantities of non-conjugated lipophilic constituents, which may have, for example, an elevated proportion of free flavonoids, free isoflavonoids, free norisoprenoids or free steroid derivatives, in this case in particular of free androstane or pregnane steroids, without the risk of non-compliance with pharmaceutical specifications. In so doing, the method according to the invention builds on the known solid-phase extraction methods, but surprisingly gets by without further extraction steps. Thus with the method according to the invention, a uniform composition of individual extract batches can be assured, since the non-conjugated lipophilic constituents, the content and composition of which in the PMU may vary according to the type of food ingested by the pregnant mares, are always eliminated and thus the extracts obtained all have a comparable content of conjugated equine estrogens relative to the dry matter. Furthermore, the separation not only of the phenolic urine contents, but in particular also of the non-conjugated lipophilic constituents in only one operating method achieved with the method according to the invention achieves a higher concentration of the active substances, i.e. of the conjugated equine estrogens, in the resulting extract.

The method according to the invention additionally also has economic advantages, since the risk of losing valuable active substances if pharmaceutical specifications are not complied with, for example in the case of insufficient contents of conjugated estrogens relative to dry matter, is considerably reduced. Furthermore, the application of the method described according to the invention permits substantially more accurate and reproducible setting of the active-substance content of the extract obtained. This active substance constituent is outstandingly suitable for the preparation of pharmaceuticals which contain a mixture of natural conjugated equine estrogens as the active substance.

The following examples are intended to illustrate the invention in further detail without limiting its scope.

EXAMPLES

In the following examples, a general operating procedure is given for obtaining active substance extracts from PMU which contain the natural mixture of the conjugated estrogens contained in the PMU and are largely depleted both in phenolic urine contents, such as, for example, cresols or HPMF, and in non-conjugated lipophilic compounds, such as, for example, non-conjugated flavonoids, non-conjugated isoflavonoids, non-conjugated norisoprenoids, non-conjugated steroids, in particular androstane and pregnane steroids, and comparable non-conjugated compounds. The examples demonstrate how a quality extract with high active-substance contents can be obtained according to the invention even from PMU which may have changing or elevated proportions of non-conjugated lipophilic compounds.

Urine:

In the method according to the invention, just as in accordance with WO 98/08526, the PMU as such, a concentrate obtained from the PMU by reduction, or a concentrate obtained from the PMU which has already been pre-purified by filtration or comparable methods may be used as the urine. The collected urine (PMU) is first freed in known manner from mucilaginous substances and solids. Advantageously, solids and mucilaginous substances are allowed to settle and then are separated using known separation methods, for example decanting, separation and/or filtering. Thus, for example, the PMU may be passed through a known separating device, e.g. a separator, a filtration unit or a sedimenter. A sand bed, for example, may serve as the separating device, or commercially available separators, e.g. nozzle or chamber separators, may be used. If desired, a microfiltration unit or an ultrafiltration unit may also be used, and if these are used it is possible to achieve a largely bacteria-free and virus-free filtered PMU at the same time.

Optionally preservatives, germicides, bactericides and/or anthelmintics may be added to the urine or the urine concentrate.

A concentrated PMU retentate which can be obtained from the PMU by known membrane filtration techniques may also be used as pre-purified urine concentrate. The solids content of the retentate and the composition thereof may vary depending on the PMU used and the membrane used for the membrane filtration, for example, the pore width thereof, and also the conditions of filtration. For example, when using a nanofiltration membrane, virtually loss-free concentration of the estrogen content in the PMU retentate can be achieved while simultaneously removing up to 50% by weight of the low-molecular PMU contents. PMU retentates which have been concentrated up to a ratio of approximately 1:10, for example a ratio of approximately 1:7, and the volume of which can thus be concentrated to approximately 1/10, for example approximately 1/7, of the original PMU volume can be used for the method according to the invention.

Adsorption Resins:

The polymeric adsorption resins usable in method step a) are, in accordance with WO 98/08526, semipolar, in particular non-ionic semipolar, polymeric adsorption resins. The polymeric adsorption resins usable as adsorbent in the method according to the invention are preferably porous organic non-ionic polymers, which in contrast to non-polar hydrophobic polymeric adsorption resins have an intermediate polarity (=e.g. with a dipole moment of the active surface of the resin in the range of 1.0 to 3.0, in particular 1.5 to 2.0, Debye) and a somewhat more hydrophilic structure, for example polycarboxylic acid ester resins. Advantageously, macroporous semipolar resins with preferably macroreticular structure and with average pore diameters in the range of 50 to 150, preferably 70 to 100, Angström and a specific surface area in the range of 300 to 900, preferably 400 to 500, $m^2/g$ are used. Macroporous cross-linked aliphatic polycarboxylic acid ester resins, in particular cross-linked polyacrylate resins such as e.g. Amberlite XAD-7 (type HP) from Rohm und Haas, which represent non-ionic semipolar adsorption resins, have proved particularly suitable.

In addition to the adsorbents named as preferred, other adsorption resins may also be used. Non-polar, semipolar and also polar adsorption resins are all suitable as adsorption resins. The amount of urine which can be pumped across the adsorber should in this case be determined beforehand by means of the respective adsorber capacity. Examples of adsorption resins which can be used are commercially available types such as polymeric Amberlite adsorbents with styrene divinylbenzene parent structures (e.g. types XAD-1180, XAD-2, XAD-16), with acrylate parent structures (e.g. XAD-7) or those with highly polar parent structures containing nitrogen and oxygen (e.g. XAD-12). Other usable adsorption resins are Dowex resins (copolymers of styrene and divinylbenzene), such as Dowex 112, Dowex Optipore, Dowex Optipore V 493; Lewatits (cross-linked polystyrenes), e.g. Lewatit OC 1064, Lewatit OC 1066 or Lewatit OC 1163, and polyamine anion-exchanger resins, e.g. Dowex resins. Advantageous adsorption resins are in particular XAD-7 (type HP), XAD-16 (type HP), XAD 118 and Dowex Optipore, preferably as Dowex Optipore V 493, and Lewatits OC 1064, OC 1066 and OC 1163.

Method Step a):

The adsorption of the conjugated estrogens on the polymeric adsorption resin can be effected in accordance with WO 98/08526 and also in the present method according to the invention by contacting the optionally treated PMU or the retentate thereof with the adsorption resin, by introducing the urine into a reactor containing the adsorption resin and keeping it in contact with the adsorption resin therein for a sufficient time for adsorption of the estrogen content. Once adsorption of the conjugated estrogens on the polymeric adsorption resin has taken place, the adsorption resin loaded with the mixture of conjugated estrogens can be separated from the rest of the urine in known manner. Advantageously, the urine can be passed through a column containing the adsorption resin at such a flow rate that the contact time is sufficient for adsorption of the estrogen content. Suitable examples are flow rates which correspond to a throughflow of 3 to 10, preferably 5 to 7, parts by volume PMU/1 part by volume adsorption resin/hour. Advantageously, the flow rate of the urine through the reactor can be controlled by operating at a slight excess pressure or partial vacuum. The amount of polymeric adsorption resin to be used may vary according to the type of adsorption resin used and the amount of the solids content in the urine. When using PMU, for example, one part by volume adsorption resin, e.g. cross-linked aliphatic polycarboxylic acid ester adsorption resin, may be loaded with up to 80, preferably from 30 to 50, parts by volume pretreated PMU, without perceptible amounts of estrogen being detectable in the discharged urine. When using a PMU concentrate or PMU retentate, the loading capacity of the adsorption resin is of course reduced to the extent by which they are concentrated. Thus for example 1 part by volume of cross-linked aliphatic polycarboxylic acid ester adsorption resin may be loaded with an amount of urine corresponding to 20 to 80, preferably 30 to 50, parts by volume PMU.

Method Step b):

The polymeric adsorption resin loaded with the mixture of conjugated estrogens is washed in method step b) with a washing water adjusted to a pH range of at least 12.0, in particular of 12.5 to 14, preferably approximately 12.5 to 13.5. Washing waters which can be used are aqueous solutions of inert basic substances soluble in the urine, which are strong enough to achieve a pH value of at least 12.5. Suitable water-soluble basic substances which are inert with respect to the polymeric adsorption resin preferably are water-soluble inorganic bases such as alkali metal or alkaline-earth metal hydroxides, in particular sodium hydroxide. Advantageously, the washing water contains only about the amount of basic substances which is required to achieve the desired pH value, preferably approximately pH 13. The amount of washing water is selected such that it is sufficient largely to remove phenolic urine contents without significant amounts of conjugated estrogens being washed out with them. For example, the use of 2 to 10, in particular 4 to 6, bed volumes washing liquid per bed volume adsorption resin has proved effective. In this case, the washing water is advantageously passed through a reactor containing the adsorption resin at a flow rate of 3 to 10, preferably 5 to 7, parts by volume washing water per 1 part by volume adsorption resin per hour.

Method Step c)—Intermediate Washing:

The polymeric adsorption resin loaded with the mixture of conjugated estrogens in method step a) is washed with water in an intermediate washing operation following method step b). The amount of washing water is selected such that the eluate obtained in the final method step e) has a mixture of conjugated estrogens which meets the requirements of a maximum content of free estrogens and thus can be used as active substance constituent for pharmaceuticals. For example, the use of 1 to 8, preferably 1 to 4, bed volumes washing water per bed volume adsorption resin has proved expedient. In this case, the washing water is advantageously passed through a reactor containing the adsorption resin at a flow rate of 3 to 10, preferably 5 to 7, parts by volume washing water per 1 part by volume adsorption resin per hour.

In one advantageous embodiment of the method according to the invention, the intermediate washing is carried out at temperatures below room temperature, in particular at temperatures between 0° C. and 10° C., since it has been shown that losses of hormone or active substance possibly due to the additional intermediate washing operation can be considerably reduced. Usually the ambient temperature is regarded as "room temperature", e.g. the term designates a temperature of between 20° and 30° C. It is very desirable to perform the method at an actual temperature of 0° C. or approximately 0° C. In practice, it is therefore recommended to operate at temperatures of close to but above 0° C. and to ensure that the aforementioned temperature ranges are maintained by suitable measures. Conventional measures for lowering the temperature may be used for this, e.g. the use of cooled reactors, cooled materials and/or cooled starting materials such as PMU. From practical points of view a temperature range from 0° C. to about 5° C., in particular of 0° C. to about 3° C., can be considered as temperatures of 0° C. or of approximately 0° C.

In order to keep any hormone losses during the intermediate washing as low as possible, according to this variant the washing water used in the intermediate washing operation and/or also the washing water which has been rendered alkaline used in method step b) will be precooled to temperatures below room temperature, in particular to temperatures between 0° C. and 10° C. Further advantageous or preferred temperature ranges are, as stated above, temperatures of 0° C. to about 5° C., in particular of from 0° C. to about 3° C. Preferably operation is at temperatures of 0° C. or of approximately 0° C., i.e. preferably the washing water used in the intermediate washing operation and/or also the washing water which has been rendered alkaline used in method step b) is precooled to temperatures close to but above 0° C. By using cooled washing water which has been rendered alkaline in method step b), a type of precooling or maintaining of the cooling of the adsorption resin which has already taken place is achieved, e.g. in order to prevent undesirable reheating of the water from taking place when using cooled washing water for the intermediate washing. Preferably, therefore, the intermediate washing and the preceding method step b) are both carried out in the same temperature range, e.g. at temperatures below room temperature, in particular at temperatures between 0° C. and 10° C., or preferably in the temperature ranges as stated above.

In the variant of the invention described above in which the method is carried out at temperatures below room temperature, it may be desirable to use all devices used, such as reactors for receiving the polymeric adsorption resin or reactors already containing same and/or the PMU used, precooled accordingly to temperatures below room temperature, in particular to temperatures between 0° C. and 10° C., or to the temperature ranges given above which are preferably to be observed.

Method Steps d), e) and f) of the Present Invention:

Then in accordance with the description in method step d) of the present invention, the washed adsorption resin loaded with the mixture of conjugated estrogens is treated with an amount of an elution liquid sufficient to elute the mixture of conjugated estrogens and in method step e) an eluate containing the natural mixture of the conjugated estrogens of the PMU is obtained and optionally concentrated or reduced. If the resulting, optionally reduced eluate represents a two-phase mixture, in a method step f) the aqueous phase of the eluate is separated, so that an aqueous phase containing the natural mixture of the conjugated estrogens of the PMU is obtained, which can optionally be further concentrated or reduced.

Regeneration of the Adsorption Resin Column

To regenerate the column, it first is washed using in each case 1 to 4, in particular 2 to 3, bed volumes of an ethanol/water mixture containing 50% ethanol and adjusted to pH 13 per bed volume of adsorption resin, then with the corresponding volume of 10%-strength aqueous sodium citrate solution, and finally with the corresponding volume of distilled water. The entire regeneration takes place at a temperature of 40° C. to 45° C. The column can be loaded and regenerated many times, for instance up to 40 times.

Example 1: Comparison example corresponding to method of WO 98/08526 and WO 03/048183

Examples 2a, 2b and 3 (method according to the invention)

Example 2a: Elution with 50% by volume ethyl acetate at room temperature

Example 2b: Elution with 50% by volume ethylacetate at 45° C.

Example 3: Elution with a one-phase ethyl acetate-containing elution mixture at 40° C.

a) Adsorption of the Estrogen Content of the PMU on a Semipolar Polyacrylate Adsorption Resin (for all Examples)

A column 330 mm high and having a diameter of 40 mm was filled with 200 ml of a semipolar polyacrylate adsorption resin (=Amberlite XAD-7 (type HP), manufactured by Rohm und Haas, grain size 0.3 to 1.2 mm, dipole moment 1.8 Debye, average pore diameter 80 Angstrom, specific surface area approximately 450 $m^2$/g dry) swollen in water. 7 l (=35 bed volumes, abbreviated hereafter as BV) of a PMU filtered through an ultrafiltration unit, the content of conjugated estrogens, calculated as total of estrone sulfate, equilin sulfate and 17 α-DH-equilin, and also of cresol, which was determined by means of HPLC (for values see Table I), was passed through the column at room temperature at a flow rate on average of 16.7 ml/min (=5 BV/h) in Example 1, 40 ml/min (=12 BV/h) in Example 2a and 24.4 ml/min (=7.3 BV/h) in Example 2b and 3. The estrogen content of the PMU was fully adsorbed on the semipolar adsorption resin column, thus loading the resin. The conjugated estrogen content of the discharged urine was measured by HPLC, and the urine proved to be practically estrogen-free. The bottom product was discarded.

b) Washing of the Loaded Adsorption Resin Column (for all Examples)

The loaded adsorption resin column was washed with 1.0 l (=5 BV) of an aqueous sodium hydroxide solution having a pH value of 13. To this end, the alkaline washing water was passed through the column at a flow rate of on average 16.7 ml/min (=5 BV/h). The conjugated estrogen and cresol contents of the exiting washing liquid were measured by HPLC. The measurements showed that during the washing phase less than 5% of the total estrogens loaded on the column was washed out.

c) Intermediate Washing (for all Examples)

The loaded adsorption resin column was washed with 600 ml water (=3 BV). To this end, the neutral washing water was passed through the column at a flow rate of on average 16.7 ml/min (=5 BV/h). The conjugated estrogen and cresol contents of the exiting washing liquid was measured by HPLC. The measurements showed that during this washing phase only a small portion (at most only about a few percent) of the total estrogens loaded on the column was washed out.

d) and e) Desorption of the Conjugated Estrogens from the Washed Adsorption Resin Column Example 1

Comparison Example 1.1 liter (=5.5 BV) of the elution liquid (ethanol/water 30:70) was passed through the column, which had been preheated to a temperature of 45° C., at an average flow rate of 8.2 ml/min (=2.4 BV/h). The discharged eluate was collected in 6 fractions E1 to E6. Each fraction was 200 ml (=1 BV) or 100 ml (=0.5 BV for E6), and the conjugated estrogen and cresol contents of each fraction were measured by HPLC (for values see Table I).

The first four fractions contained approximately 80 to 98% of the entire amount of conjugated estrogens adsorbed on the column. The final fractions contained only a small amount of conjugated estrogens. The fractions containing the bulk of the conjugated estrogens represent extracts suitable for galenic further processing.

Example 2

2a) Elution with 50% by Volume Ethyl Acetate at Room Temperature

2b) Elution with 50% by Volume Ethyl Acetate at 45° C.

900 ml (=4.5 BV) of the two-phase elution liquid (ethyl acetate/water mixture in a ratio of 50:50) was passed at an average flow rate of 16.7 ml/min (=5.0 BV/h) through the column set to the given elution temperature. The exiting eluate was collected in 9 fractions E1 to E9. The fractions were each 100 ml (0.5 BV) from the fourth fraction onwards, a two-phase mixture was obtained as eluate which—for the purpose of individual analysis of each eluate—was separated into the aqueous and organic phases (E4 to E9, in each case LM for solvent and W for aqueous phase). The conjugated estrogen and cresol contents of all fractions were measured by HPLC (for values see Table I). For some fractions, the content of non-conjugated lipophilic compounds, for example formononetin, also was determined by gas chromatography (GC) (for values see Table II).

The first three fractions contained only traces of estrogens. Approximately 80 to 98% of the entire amount of conjugated estrogens adsorbed on the column were then contained in the aqueous phases of the following fractions 4 to 8. The final fractions contained only small amounts of estrogens. The fractions containing the bulk of the conjugated estrogens represent extracts suitable for galenic further processing.

To check the completeness of the elution according to the invention with the ethyl acetate/water mixture, the already known extraction with the one-phase ethanol/water mixture (30:70) followed the extraction.

In Example 2a, however, considerable amounts of conjugated estrogens, corresponding to approximately 6.8% of the amount charged, were eluted by the subsequent ethanolic elution. By increasing the elution temperature to 45° C., it was possible to reduce the amount of the conjugated estrogens still remaining on the column, which were not eluted until the ethanolic elution, to less than 1%.

Example 3

Elution with a One-Phase Ethyl Acetate-Containing Elution Mixture at 40° C.

1.0 ml (=5 BV) of the one-phase elution liquid (ethyl acetate/water/acetone mixture in a volume ratio of 1:1:1.4) was passed at an average flow rate of 16.7 ml/min (=5.0 BV per hour) through the column set to 40° C. The exiting eluate was collected in 13 fractions of different sizes. The first fraction was 100 ml (=0.5 BV), the following 10 fractions were each 50 ml (=0.25 BV), whereas the last two fractions were 200 ml each. After the displacement of the washing water from the column, surprisingly two phases already appeared in the eluate (from fraction 4 onwards). The conjugated estrogen and cresol contents of all fractions were measured by HPLC (for values see Table I).

The first fraction contained only traces of estrogens. Approx. 80 to 98% of the entire amount of conjugated estrogens adsorbed on the column were then contained in the following fractions 2 to 7. The final fractions contained only small amounts of estrogens. The fractions containing the bulk of the conjugated estrogens represent extracts suitable for galenic further processing.

Eluates E7 to E13 separated into 2 phases only after approximately 24 hours. Eluates E1 to E7 were combined and worked up as follows: Eluates E1-E7 were combined in a 500 ml dropping funnel and yielded approximately 350 ml solution. No immediate phase separation took place, but after being left to stand over the weekend, a small organic phase of approx. 10 ml was visible at the top of the dropping funnel. The conjugated estrogen and cresol contents of the phases were measured by HPLC. After separation of the phases, the aqueous phase was concentrated in a rotary evaporator at 70° C. to a DM of 8-10% (here 8.16% DM, for values see Table I). Regeneration of the Adsorption Resin Column (for all Examples)

To regenerate the column, it was first washed with 400 ml of an ethanol/water mixture containing 50% ethanol and adjusted to pH 13, then with 400 ml 10%-strength aqueous sodium citrate solution, and finally with 400 ml distilled water. The entire regeneration took place at a temperature of 40° C. to 45° C. The column can be loaded and regenerated many times, for instance up to 40 times.

For each of the fractions obtained by the elution and containing the bulk of the conjugated estrogens, the DM content in % by weight and the contents determined by HPLC of conjugated estrogens (CO calculated as the total of sodium estrone sulfate, sodium equilin sulfate and 17 α-DH-equilin) and also of cresol are given in the following table. Furthermore, the yield of the extraction is listed as a value.

TABLE I

Comparison of the individual methods using the composition of the fractions containing the bulk of the conjugated estrogens

| | Vol [l] | DM weight. % | Cresol [mg/l] | 17α-DH-Equ. [mg/l] | Equilin [mg/l] | Estrone [mg/l] | CO [mg/l] | CO mg | CO weight. % DM | Yield |
|---|---|---|---|---|---|---|---|---|---|---|
| | | | | Example 1-comparison method | | | | | | |
| PMU | 7.0 | n.d. | 329 | 25.3 | 57.9 | 64.9 | 148.1 | 1037 | n.d. | |
| E1 | 0.2 | 0.22 | 0.0 | 21.2 | 65.8 | 76.0 | 163.0 | 33 | 7.46 | |
| E2 | 0.2 | 1.08 | 0.0 | 345.9 | 1093.8 | 1237.0 | 2676.7 | 535 | 24.77 | |
| E3 | 0.2 | 0.44 | 0.0 | 183.4 | 524.7 | 607.8 | 1315.9 | 263 | 30.24 | |
| E4 | 0.2 | 0.10 | 0.0 | 30.2 | 58.2 | 84.6 | 173.0 | 35 | 16.99 | |
| E5 | 0.2 | 0.06 | 8.9 | 7.5 | 21.1 | 37.5 | 8 | 6.49 | | |
| E2-4* | 0.6 | 0.54 | 0.0 | 186.5 | 558.9 | 643.1 | 1388.5 | 833 | 25.71 | 80% |
| | | | | Example 2a-elution with water/ethyl acetate 50:50 at RT | | | | | | |
| PMU | 7.0 | n.d. | 163.0 | 15.7 | 41.1 | 71.1 | 127.9 | 895 | n.d. | |
| E3 | 0.1 | 0.29 | 0.0 | 90.1 | 254.8 | 379.8 | 724.7 | 72 | 24.99 | |
| E4 W | 0.064 | 2.70 | 266.0 | 735.5 | 1877.7 | 2858.2 | 5471.5 | 350 | 20.24 | |
| E5 W | 0.053 | 1.00 | 188.8 | 466.9 | 1233.9 | 1877.4 | 3578.2 | 190 | 35.84 | |
| E6 W | 0.051 | 0.50 | 98.9 | 245.6 | 666.9 | 1015.1 | 1927.6 | 98 | 38.68 | |
| E7 W | 0.051 | 0.31 | 57.8 | 136.2 | 363.8 | 551.7 | 1051.7 | 54 | 33.82 | |
| E8 W | 0.051 | 0.23 | 33.8 | 79.6 | 208.0 | 314.4 | 602.0 | 31 | 26.27 | |
| E4-8* | 0.27 | 1.02 | 136.1 | 353.1 | 921.3 | 1401.4 | 2675.8 | 722 | 25.91 | 81% |
| | | | | Example 2b-elution with water/ethyl acetate 50:50 at 45° C. | | | | | | |
| PMU | 7.0 | n.d. | 549.1 | 13.5 | 61.3 | 56.3 | 131.0 | 917 | n.d. | |
| E3 | 0.1 | n.d. | 31.8 | 26.6 | 124.4 | 122.7 | 273.7 | 27 | n.d. | |
| E4 W | 0.086 | 2.67 | 0.0 | 401.9 | 1719.9 | 1684.2 | 3806.0 | 327 | 14.25 | |
| E5 W | 0.058 | 1.49 | 0.0 | 519.8 | 2527.0 | 2268.4 | 5315.1 | 308 | 35.67 | |
| E6 W | 0.058 | 0.60 | 0.0 | 227.1 | 878.3 | 884.1 | 1989.6 | 115 | 33.16 | |
| E7 W | 0.056 | 0.25 | 0.0 | 84.9 | 350.7 | 357.9 | 793.6 | 44 | 31.74 | |
| E8 W | 0.053 | 0.19 | 0.0 | 50.4 | 208.1 | 204.2 | 462.8 | 25 | 24.36 | |
| E4-8* | 0.311 | 1.21 | 0.0 | 274.3 | 1209.3 | 1152.9 | 2636.5 | 820 | 21.87 | 89% |
| | | | | Example 3-elution with water/ethyl acetate/acetone 10:10:14 at 40° C. | | | | | | |
| PMU | 7.0 | n.d. | 266.4 | 31.9 | 71.7 | 91.5 | 195.0 | 1365 | n.d. | |
| E1 | 0.1 | 0.30 | 0.0 | 58.4 | 126.2 | 180.8 | 365.3 | 37 | 12.18 | |
| E2 | 0.05 | 0.28 | 0.0 | 75.9 | 194.2 | 272.8 | 542.8 | 27 | 19.39 | |
| E3 | 0.05 | 1.40 | 0.0 | 794.0 | 1834.5 | 2304.5 | 49330 | 247 | 35.24 | |
| E4 W | 0.046 | 4.24 | 0.0 | 2300.5 | 5446.5 | 6947.8 | 14694.8 | 676 | 34.66 | |
| E5 W | 0.035 | 1.68 | 0.0 | 745.8 | 1722.8 | 2165.0 | 4633.5 | 162 | 27.58 | |
| E6 W | 0.035 | 0.57 | 0.0 | 212.5 | 454.0 | 548.5 | 1215.0 | 43 | 21.32 | |
| E7 | 0.05 | 0.03 | 0.0 | 81.0 | 166.5 | 212.0 | 459.5 | 23 | — | |
| E8 | 0.05 | 0 | 0.0 | 9.6 | 20.1 | 25.0 | 54.7 | 3 | — | |
| E1-7* | 0.366 | 1.06 | 0.0 | 526.6 | 1227.0 | 1563.1 | 3316.8 | 1214 | 31.29 | 89% |
| E1-7W | 0.34 | 1.06 | 0.0 | 508.0 | 1146.6 | 1516.8 | 3171.4 | 1078 | 29.91 | 79% |
| E1-7L | 0.01 | n.d. | 0.0 | 97.0 | 235.0 | 340.0 | 672.0 | 7 | — | |
| E1-7W conc. | 0.044 | 8.16 | 0.0 | 3878 | 8798 | 11780 | 24456 | 1076 | 29.97 | 79% |

*contents determined by computer.

With a test performed as in Example 1, i.e. for an ethanolic elution, a portion of the isoflavones, for example equol, is washed out with the basic washing, a portion of the isoflavones, for example formononetin, however passes into the eluate, and can only be separated by a subsequent extraction. Something similar applies for other non-conjugated lipophilic compounds, such as for example free steroid hormones. In contrast, with the elution method according to the invention the isoflavones and free steroids still on the column pass predominantly into the non-water-miscible solvent phase of the optionally reduced eluate, whereas approx. 98% of the conjugated estrogens is found in the aqueous phase of this eluate which is to be processed further. This aqueous phase is free of non-conjugated steroid hormones and largely depleted in isoflavones and comparable non-conjugated lipophilic compounds. This distribution is made clear by GC analysis of the aqueous phase and the organic phase of the 4th eluate of Example 2a, as can be gathered from the following Table II:

TABLE II

Distribution of the conjugated estrogens, the free steroid hormones and the formononetin (as example of isoflavones) in the aqueous phase and the organic solvent phase of the 4th eluate of Example 2a - Evaluation of the GC analysis (the aqueous phase was concentrated by approximately 1.8 times before determination):

| Eluate 4 Phase | Weight [g] | CO (total) | | | | Free hormones | | | Formononetin | | |
|---|---|---|---|---|---|---|---|---|---|---|---|
| | | [mg/g] | [mg] | % proportion | | [mg/g] | [mg] | % proportion | [mg/ml] | [mg] | % proportion |
| Water | 34.1 | 9.16 | 312 | 97.9 | | 0 | 0 | 0 | 0.027 | 0.9 | 45.2 |
| Ethyl acetate | 30.5 | 0.23 | 7 | 2.1 | | 0.072 | 2.1 | 100 | 0.037 | 1.1 | 54.8 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variation within the scope of the appended claims and equivalents thereof.

What is claimed is:

1. A method for obtaining a natural mixture of conjugated estrogens from pregnant mares' urine, comprising:
   contacting a urine with an amount of a polymeric adsorption resin sufficient to adsorb the mixture of conjugated estrogens contained in the urine, and separating a resulting polymeric adsorption resin loaded with the mixture of conjugated estrogens from the rest of the urine;
   washing the polymeric adsorption resin loaded with the mixture of conjugated estrogens with a washing water which has been adjusted to a pH value of at least 12.0;
   contacting the washed adsorption resin with a sufficient amount of an elution liquid to desorb the mixture of conjugated estrogens loaded thereon,
   wherein the elution liquid is a one-phase or two phase mixture containing:
   (i) water,
   (ii) at least one water-immiscible or only slightly water-miscible organic solvent suitable for the elution of the non-conjugated lipophilic compounds selected from the group consisting of non-conjugated flavonoids, non-conjugated isoflavonoids, non-conjugated norisoprenoids, and non-conjugated steroids, and which organic solvent is selected from the group consisting of straight-chain, branched or cyclic $C_4$-$C_{10}$ alcohols, $C_1$-$C_{10}$ esterified acids, $C_3$-$C_{10}$ aldehydes, $C_4$-$C_{10}$ ketones, $C_3$-$C_{10}$ ethers, $C_3$-$C_6$ nitriles, $C_1$-$C_3$ haloalkanes, and mixtures of two or more of the foregoing solvents; and
   (iii) at least one water-miscible organic solvent selected from the group consisting of water-miscible ethers, lower alkanols, lower aliphatic ketones, and mixtures of two or more of the foregoing solvents;
   separating an eluate containing the natural mixture of conjugated estrogens from the adsorption resin;
   wherein the natural mixture of conjugated equine estrogens obtained is depleted in phenolic urine contents and in non-conjugated lipophilic compounds selected from the group consisting of non-conjugated flavonoids, non-conjugated isoflavonoids, non-conjugated norisoprenoids, and non-conjugated steroids;
   and if the separated eluate is a two-phase mixture, further comprising separating the phases and recovering an aqueous phase containing the natural mixture of conjugated estrogens.

2. A method according to claim 1, wherein the starting urine is a urine freed of mucilaginous substances and solids, a reduced concentrate of such a urine, or a reduced urine retentate obtained by membrane filtration of such a urine.

3. A method according to claim 1, wherein the polymeric adsorption resin loaded with the mixture of conjugated estrogens subjected to an intermediate washing with water between the washing with water which has been adjusted to a pH of at least 12.0 and the contacting with the elution liquid.

4. A method according to claim 1, wherein the water in the elution liquid is adjusted to a pH value in the alkaline range.

5. A method according to claim 1, further comprising reducing the volume of the separated eluate.

6. A method according to claim 1, wherein the organic solvent in (ii) is selected from the group consisting of $C_1$-$C_4$-alkyl acetates, butanol, cyclohexanol, hexanol, diethyl ether, methylene chloride, methyl tert, butyl ether, and mixtures of two or more of the forgoing.

7. A method according to claim 6, wherein the organic solvent in (ii) is selected from the group consisting of $C_1$-$C_4$-alkyl acetates and mixtures thereof.

8. A method according to claim 7, wherein the organic solvent in (ii) is ethyl acetate, isopropyl acetate, or a mixture thereof.

9. A method according to claim 1, wherein the water-miscible organic solvent is selected from the group consisting of acetone, ethanol, tetrahydrofuran, and mixtures of two or more of the foregoing.

10. A method according to claim 9, wherein the water-miscible organic solvent is acetone, ethanol, or a mixture thereof.

11. A method according to claim 10, wherein the water-miscible organic solvent is acetone.

12. A method according to claim 1, wherein the organic solvent in (ii) is selected from the group consisting of $C_1$-$C_4$-alkyl acetates and mixtures thereof, and wherein the water-miscible organic solvent in (iii) is acetone, ethanol or a mixture thereof.

13. A method according to claim 12, wherein the organic solvent in (ii) is ethyl acetate, isopropyl acetate, or a mixture thereof.

14. A method according to claim 12, wherein the organic solvent in (ii) is ethyl acetate, and the water-miscible organic solvent in (iii) is acetone.

15. A method according to claim 1, wherein the elution liquid comprises water and water-immiscible or only slightly water-miscible organic solvent in a volume ratio of water to organic solvent of from 5:1 to 1:5.

16. A method according to claim 15, wherein the volume ratio of water to water-immiscible or only slightly water-miscible organic solvent is from 2:1 to 1:2.

17. A method according to claim 1, wherein the elution liquid comprises water and water-miscible organic solvent in a water to water-miscible organic solvent volume ratio of from 4:1 to 1:5.

18. A method according to claim 17, wherein the water to water-miscible organic solvent ratio is from 2:1 to 1:3.

19. A method according to claim 1, wherein the water, water-immiscible or slightly water-miscible organic solvent, and water-miscible organic solvent in the elution liquid are present in amounts such that the ratio of the sum of the volumes of the water and water-immiscible or slightly water-miscible organic solvent to the volume of water-miscible organic solvent is from 5:1 to 1:5.

20. A method according to claim 19, wherein the ratio of the sum of the volumes of the water and the water-immiscible or slightly water-miscible organic solvent to the volume of the water-miscible organic solvent is from 2:1 to 1:2.

21. A method according to claim 12, wherein the elution liquid comprises water; at least one $C_1$-$C_4$-alkyl acetate; and acetone, ethanol or a mixture thereof in a volume ratio of from 1:1:1 to 1:1:2.

22. A method according to claim 12, wherein the volume ratio of water; at least one $C_1$-$C_4$-alkyl acetate; and acetone, ethanol or a mixture thereof is about 1:1:1.4.

23. A method according to claim 1, wherein the polymeric adsorption resin is a semipolar adsorption resin.

24. A method according to claim 23, wherein the polymeric adsorption resin is a non-ionic, semipolar adsorption resin.

25. A method according to claim 1, wherein the elution of the mixture of conjugated estrogens from the washed adsorption resin is carried out at temperatures in the range from 20° C. to 80° C.

26. A method according to claim 25, wherein the elution is carried out at temperatures in the range from 30° C. to 50° C.

* * * * *